(12) United States Patent
Greenberg et al.

(10) Patent No.: US 8,734,435 B2
(45) Date of Patent: May 27, 2014

(54) DUAL PORT ABLATION CANNULA AND KIT

(71) Applicants: Steven M. Greenberg, Boca Raton, FL (US); Scott S. Katzman, Port St. Lucie, FL (US)

(72) Inventors: Steven M. Greenberg, Boca Raton, FL (US); Scott S. Katzman, Port St. Lucie, FL (US)

(73) Assignee: Orthopaedic Development LLC, Lake Worth, FL (US)

( * ) Notice: Subject to any disclaimer, the term of this patent is extended or adjusted under 35 U.S.C. 154(b) by 17 days.

(21) Appl. No.: 13/770,859

(22) Filed: Feb. 19, 2013

(65) Prior Publication Data
US 2013/0267938 A1 Oct. 10, 2013

Related U.S. Application Data

(60) Continuation-in-part of application No. 11/101,221, filed on Apr. 7, 2005, now Pat. No. 8,376,931, which is a division of application No. 10/278,405, filed on Oct. 23, 2002, now Pat. No. 6,902,526.

(51) Int. Cl.
*A61B 18/18* (2006.01)

(52) U.S. Cl.
USPC .......... 606/13; 606/16; 606/79; 606/167; 606/170; 606/176; 600/104; 600/108; 600/129; 600/130

(58) Field of Classification Search
USPC ......... 606/1, 13–16, 53, 79, 88–90, 167, 170, 606/176, 179; 600/101, 104, 108, 109–114, 600/123, 128–130, 153, 156, 160
See application file for complete search history.

(56) References Cited

U.S. PATENT DOCUMENTS

| 6,258,083 B1 * | 7/2001 | Daniel et al. | 606/15 |
| 6,572,563 B2 * | 6/2003 | Ouchi | 600/564 |
| 8,376,931 B2 * | 2/2013 | Katzman | 600/104 |

* cited by examiner

*Primary Examiner* — Ahmed Farah
(74) *Attorney, Agent, or Firm* — Steven M. Greenberg, Esq.; CRGO Law

(57) ABSTRACT

A dual port ablation cannula kit includes a trocar and a hollow shaft defining a longitudinal lumen. The shaft has a proximal segment and a distal segment, such that the distal segment includes a distal tip substantially aligned with the shaft to permit passage of the trocar within the hollow shaft. The distal tip also is configured with a tissue-gripping surface in as much as a plane of the tissue-gripping surface is substantially perpendicular to a longitudinal axis of the shaft, dual ports extending from an exterior surface of the hollow shaft, each port defining a hollow passageway into the hollow shaft, and dual couplers, one coupling a suction line to one of the dual ports and another coupling an irrigation line to another of the dual ports. Finally, the kit can include a laser fiber.

9 Claims, 3 Drawing Sheets

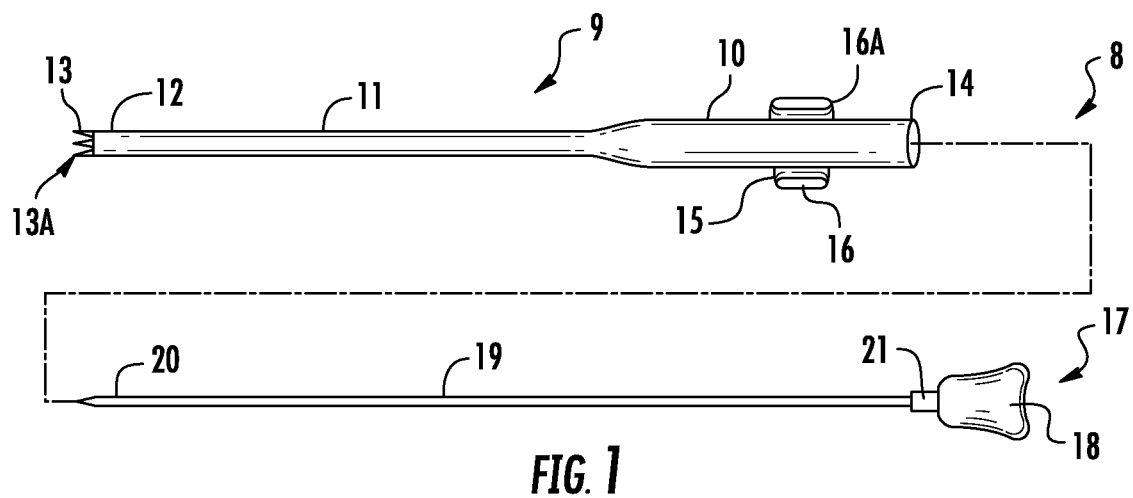
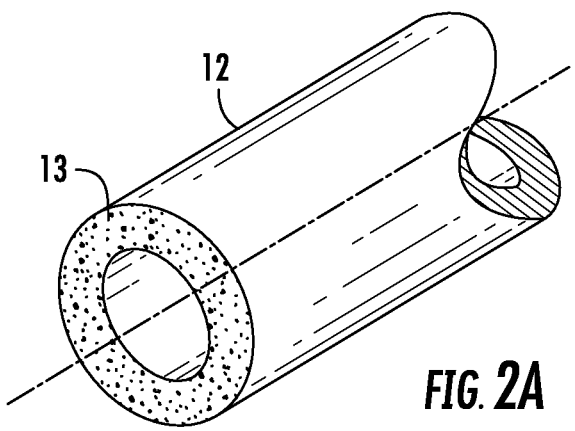
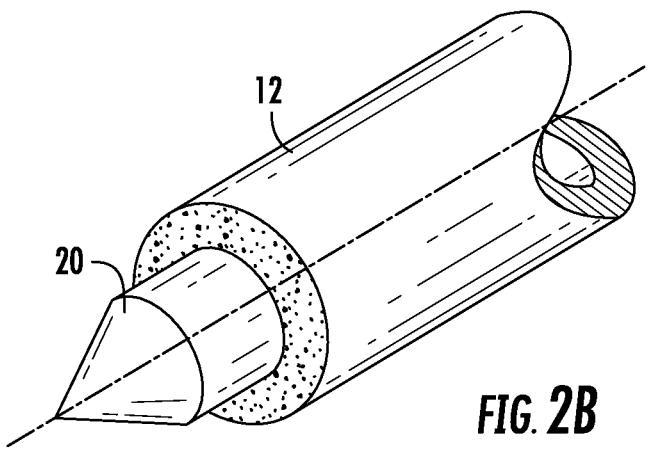

US 8,734,435 B2

DUAL PORT ABLATION CANNULA AND KIT

CROSS REFERENCE TO RELATED APPLICATIONS

This patent application claims the benefit under 35 U.S.C. §121 as a continuation in part of U.S. patent application Ser. No. 11/101,221, filed Apr. 7, 2005 now U.S. Pat. No. 8,376,931 entitled VISUALIZING ABLATION CANNULA, the entire teachings of which are incorporated herein by reference.

BACKGROUND OF THE INVENTION

1. Field of the Invention

The disclosed invention is in the field of medical devices and procedures. In particular, the disclosed invention pertains to a novel surgical device and its use for ablation of tissues associated with solid anatomical surfaces such as joints.

2. Description of the Related Art

Lower back pain (LBP) is a common musculoskeletal complaint of industrialized society with a reported 60-90% of the population experiencing at least one episode of LPB per lifetime. As such, LBP is a very common cause of disability in persons younger than 45 years, the second leading reason for visits to primary care physicians, and the most frequent cause of visits to orthopedic surgeons and neurosurgeons. As the most frequently reported work-related injury, LBP is the most costly of all medical diagnoses when the costs of time lost at work, long-term disability and medical and legal expenses are factored in. Over the past century, various structures associated with the spine and back muscles, including the dorsal root ganglia, dura, muscles of the lumbar spine and the facet joints, have been implicated as the source of chronic LBP. Many recent clinical studies implicate facet joints of the spine as the source of pain in LBP. The spine is composed of a series of functional units, each consisting of an anterior segment made up of two adjacent vertebral bodies and the intervertebral disc between them, and the posterior segment consisting of the laminae and their processes. Bones of the spine articulate anteriorly by intervertebral discs and posteriorly by paired joints. The paired joints, known as the facet or zygapophyseal joints, are formed by the articulation of the processes on the laminae of adjacent vertebrae. Thus the superior articular process of one vertebra articulates with the inferior articular process of the vertebra below to form the facet joint.

Facet joints are true synovial joints with a joint space, hyaline cartilage surfaces, a synovial lining, and a fibrous capsule. Nociceptive (pain-sensing) nerve fibers and autonomic nerves have been identified in the lumbar facet joint capsule and synovial folds in recent studies. Inflammation, injury, nerve entrapment and degenerative osteoarthritic changes in the joint tissues all can lead to pain originating in the facet joints. Facet joint pain may also arise secondary to vertebral disc degeneration, owing to facet-joint osteoarthritis that develops in response to the primary disc degeneration.

Pain cannot be felt if the nerve pathways that relay pain impulses to the brain are interrupted. Painful stimuli from the facet joints are carried by the medial branches of the dorsal primary rami. On the theory that facet joint-mediated LBP should not be perceived in absence of intact medial nerve pathways, denervation (neurotomy) of the dorsal medial nerve branch has been advocated for treatment of lumbar facet joint pain. Early methods included destruction of the nerves by injection of neurolysing agents; however in recent years radiofrequency (RF) ablation of these nerves is the most widely used technique for denervation of the facet joints.

The target of a needle used for facet joint nerve ablation in the lumbar region (L1-L4 levels) is the portion of the nerve on the dorsal surface of the transverse process just caudal to the most medial end of the superior edge of the transverse process. The approximate vicinity of the target nerves can be determined using fluoroscopic techniques in subjects lying prone on a fluoroscopy table. Specifically, in the RF ablation procedure, under radiographic guidance, an introducer cannula is positioned in the vicinity of the dorsal medial nerve. Ideally the cannula is positioned alongside the nerve, rather than with its point facing the nerve. Once the position of the cannula appears to be correct, based on the radiographic image and the "feel" of the target tissue, the surgeon introduces an RF electrode via the cannula, with the aim of positioning the electrode alongside the nerve. Following positive stimulation at low voltage that reproduces the subject's pain, an RF lesion is created by passing current through the electrode that raises the tissue temperature to 60-80 degrees centigrade for 60-90 seconds. This portion of the procedure is quite uncomfortable and calls for judicious use of sedation and analgesics.

Existing devices such as RF probes used for denervation of facet joints are placed by surgeons using radiographic techniques (C-arm fluoroscopy) without the benefit of endoscopic guidance to ensure accurate positioning of the electrodes. In fact, proper placement of the needle tip in the complicated structure of a subject's spine requires great skill by the treating clinician. The needles may need to be withdrawn and re-inserted multiple times. Errors in needle placement and in particular, the slippage of the needle once placed off the facet joint can result in accidental impalement of structures such as the nerve root in the lower spine, presenting a serious medical risk to the subject.

The success of RF denervation procedures varies widely, with a lower end of 9%. Despite improvements in technological approaches and controls incorporated into later clinical assessments of the efficacy of facet joint denervation as a therapy for LBP, there continues to be a wide range of reported success rates. This wide variability in the procedure in the hands of different practitioners suggests unpredictability inherent in the procedure itself. The unpredictability may be a reflection of failure of existing methods to enable sufficiently precise and stabilize localization of the target nerve prior to lesioning, combined with incomplete destruction of the pain-causing nerve fibers by the RF electrode.

BRIEF SUMMARY OF THE INVENTION

Embodiments of the present invention address deficiencies of the art in respect to facet joint ablation needles and provide a novel and non-obvious dual port ablation cannula kit. The kit includes a trocar and a hollow shaft defining a longitudinal lumen. The shaft has a proximal segment and a distal segment, such that the distal segment includes a distal tip substantially aligned with the shaft to permit passage of the trocar within the hollow shaft. The distal tip also is configured with a tissue-gripping surface in as much as a plane of the tissue-gripping surface is substantially perpendicular to a longitudinal axis of the shaft. The shaft also includes dual ports extending from an exterior surface of the hollow shaft, each port defining a hollow passageway into the hollow shaft. Dual couplers also can be provided, one of the couplers coupling a suction line to one of the dual ports and another of the coupler coupling an irrigation line to another of the dual ports. Finally, the kit can include a laser fiber that includes a diameter less than an interior diameter of the hollow shaft so as to permit passage of the laser fiber through the hollow shaft.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

There are shown in the drawings embodiments which are presently preferred, it being understood, however, that the invention is not limited to the precise arrangements and instrumentalities shown, wherein:

FIG. 1 is a schematic side elevation illustrating a dual port ablation needle including a cannula with a tissue-gripping distal tip and a trocar with a pointed tip;

FIGS. 2A and 2B, taken together, are perspective views of a dual port ablation needle from the perspective of the distal tip;

DETAILED DESCRIPTION OF THE INVENTION

Figure 3:
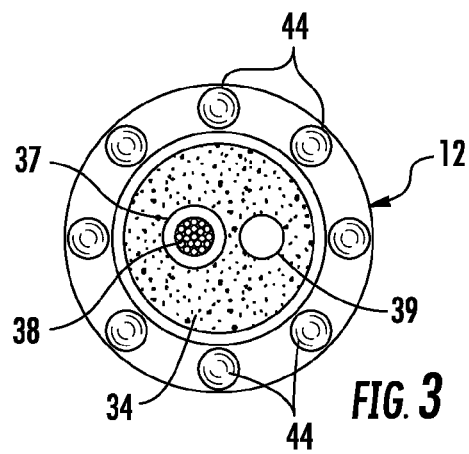
FIG. 3 is an end-on view of the distal tip of dual port ablation needle having a visualizing ablation probe inserted therein.

The present invention is a medical apparatus and surgical procedure for the ablation of tissue in a subject's body. The apparatus can include a dual port ablation needle kit. The kit includes a dual port ablation cannula with a tissue gripping surface at a distal end of the cannula and two different ports extending from an exterior surface of the cannula and each providing a passageway into the cannula. The kit also can include a trocar and a laser fiber configured for coupling to one port of the dual port ablation cannula. In use, an irrigation source can be connected to the cannula by way of one of the ports, and a suction device can be connected to the cannula by way of the other of the ports. The cannula can be placed at a tissue site requiring treatment, and the trocar can be included within the cannula to occlude the cannula during placement. Once the cannula has been positioned within the subject's body proximate to the target tissue, the cannula can grip the target tissue with the tissue gripping surface and the laser fiber can be inserted into the cannula to ablate the target tissue during treatment with a medical laser.

Referring initially to FIG. 1, several features of the kit of the invention are shown, including an embodiment of the dual port cannula with a distal tip 12 having a tissue-gripping surface 13. The tissue-gripping surface can include triangularly shaped teeth 13A. FIG. 1 also depicts an embodiment of the trocar 17 with a pointed tip 20. In the illustrated embodiment of the cannula, the shaft 9 can be a hollow tube having a proximal segment 10 wider than the distal segment 11. In other embodiments, the proximal segment 10 can be narrower than the distal segment 11, or of the same dimensions. The shaft 9 also can include dual ports 16 and 16A. Each of the ports 16 and 16A can define a passageway from an exterior of the shaft 9 to an interior portion of the hollow tube defined by the shaft 9. Further, each of the ports 16 and 16A can include threads 15 to permit coupling of respectively different couplers each adapted to connect an irrigation line and a suction line, respectively to the ports 16 and 16A.

The lengths of the proximal and distal segments of the shaft 9 can be varied according to the particular application. For example, in a specific embodiment of the invention useful for denervation of facet joints, the narrower distal segment of the cannula shaft 9 can be the only portion inserted into the subject's body. The "working distance" available for insertion of the cannula beneath the skin can be determined by the length of the distal segment 11. As noted, a tissue-gripping surface 13 with teeth 13A can be disposed at the distal tip of the shaft 9.

This feature may be better appreciated in FIG. 2A, which shows a perspective view of the cannula distal tip 12, viewed from the distal end. The plane of the tissue-gripping surface can be perpendicularly positioned relative to the axis of the shaft, as in the particular embodiment shown in FIG. 2A, but other orientations of this surface are included within the invention. The tissue-gripping components can include teeth that protrude from the end of the shaft. In a specific embodiment shown in FIG. 3, eight teeth 44 are evenly spaced about the circumference of the wall of the cannula shaft in a crown arrangement; however many other numbers, shapes and arrangements of teeth, or other protrusions or surfaces capable of adhering to tissues, can be envisioned and are within the scope of the invention.

Referring again to FIG. 1, the proximal segment of the shaft 9 can be open at its proximal end 14. The proximal end 14 can be suitably fitted for attachment of components of the needle set designed for insertion into the lumen of the cannula shaft, e.g. the trocar 17 and the visualizing ablation probe. For example, in some embodiments of the invention, the interior of the proximal end 14 includes threading complementary to that on the trocar, enabling the trocar to be secured to the cannula by screwing it into the proximal end 14. Other means of attaching needle components to one another are known and can be used in the invention.

The cannula kit further includes a trocar 17 configured for insertion into the shaft 9 through the opening in the proximal end 14. As seen in FIG. 1, the trocar 17 includes a handle 18, a shaft 19 and a tip 20 which is closed. The function of the trocar is to occlude the lumen of the shaft 9, thereby preventing the lumen from clogging with tissue during advancement of the shaft 9 through the subject's body. As indicated by the dotted line 8 in FIG. 1, the trocar can be inserted into the shaft 9 and secured to the proximal end 14 by a connecting means 21 on the trocar handle. The trocar 17 and shaft 9 are designed to be used as a set, with the trocar shaft 19 configured for inclusion within the lumen of the corresponding shaft 9.

In some embodiments of the invention, it is desirable to have a trocar 17 with a point at its tip 20, to facilitate penetration of the needle set through the subject's tissues. In such needle sets, the length of the trocar shaft 19 can be longer than that of the cannula shaft 9, such that the point on the trocar 17 protrudes beyond the distal tip of the shaft 9 when the trocar 17 is secured in place within the shaft 9. FIG. 2B is a schematic diagram showing protrusion of a pointed trocar tip 20 from a cannula distal tip 12.

Figure 4:
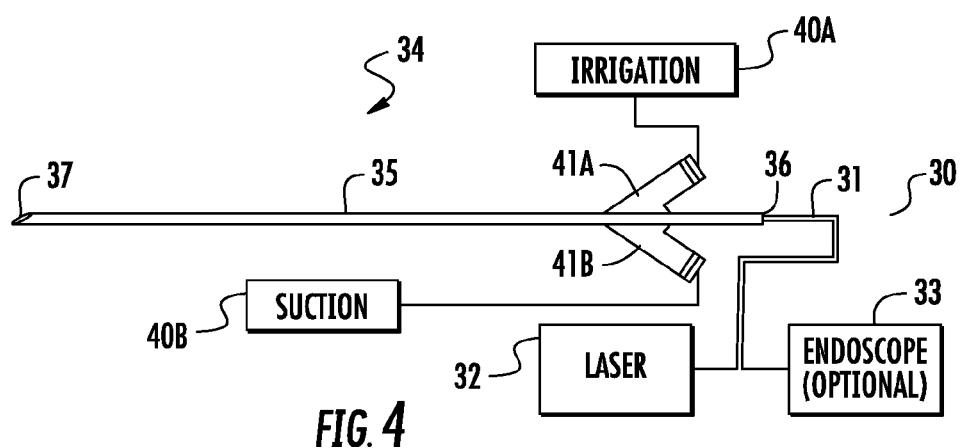
FIG. 4 is a schematic diagram of a dual port, visualizing ablation probe configured with an obturator and tools connected to an endoscope, a laser, irrigation and suction; and, FIG. 5 is a flowchart illustrating a procedure for facet joint tissue ablation utilizing a dual port ablation needle kit.

FIG. 4 is a schematic diagram of a visualizing dual port ablation kit 30. As discussed previously, a probe 31 can be coupled to a laser energy source 32 and, optionally, to an endoscope 33 such that the probe 31 either includes a laser fiber, or a combination of laser fiber and endoscope camera. The visualizing ablation probe 31 can be inserted into a cannula shaft 35 that includes an obturator 34 configured for inclusion in the cannula shaft 35. The obturator 34 enables the laser fiber and endoscope camera to be passed to the distal end 37 of the cannula shaft 35, adjacent to the site of tissue treatment. Finally, dual ports 41A and 41B can be affixed to an outer surface of the shaft 35 and can provide a passageway to an interior portion of the shaft 35. The port 41A can be coupled to an irrigation source 40A and the port 41B can be coupled to a suction device 40B.

Figure 6:
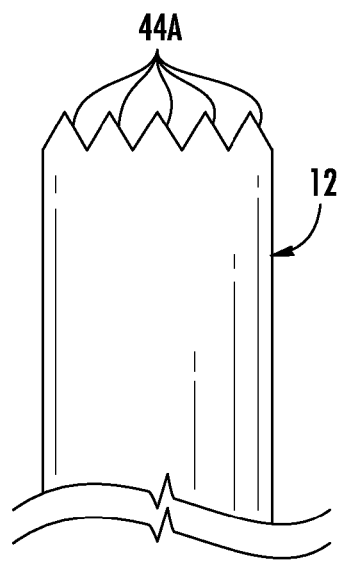
FIG. 6 is an exploded view of a distal end of a dual port ablation needle showing teeth of the tissue gripping surface; and, FIG. 7 is a perspective view of a dual port ablation needle kit with an irrigation and laser fiber aggregation point.

In some embodiments of the obturator, the plane of the distal end 37 can be at right angles to the longitudinal axis of the shaft 35. In the specific embodiment shown in FIG. 4, the distal end 37 can be cut to include a tissue gripping surface such as that shown in FIG. 6. In FIG. 6, the distal tip 12 is shown to include a set of teeth 44A protruding longitudinally from the distal tip 12. Optionally, each of the teeth 44A can be slightly angled inwards towards a vertex defined by a circumference of the distal tip 12 so as to inhibit a cutting action of the teeth 44A.

Referring now to an end-on view of the distal tip of the invention shown in FIG. 3, the configuration of the needle set is seen when a visualizing ablation probe is inserted into the lumen of the cannula. In the specific illustrative embodiment shown, the obturator 34 contains two longitudinal channels. A laser endoscope channel 37 can be provided for passage of a bundled cable 38 containing both an endoscopic camera lens and a laser ablation tool. An injection channel 39 can be provided to enable delivery of a solution such as an anesthetic or an irrigation solution directly to the site of tissue ablation. The number, size and cross-sectional shape of the longitudinal channels in the obturator can be varied according to the particular application.

Figure 5:
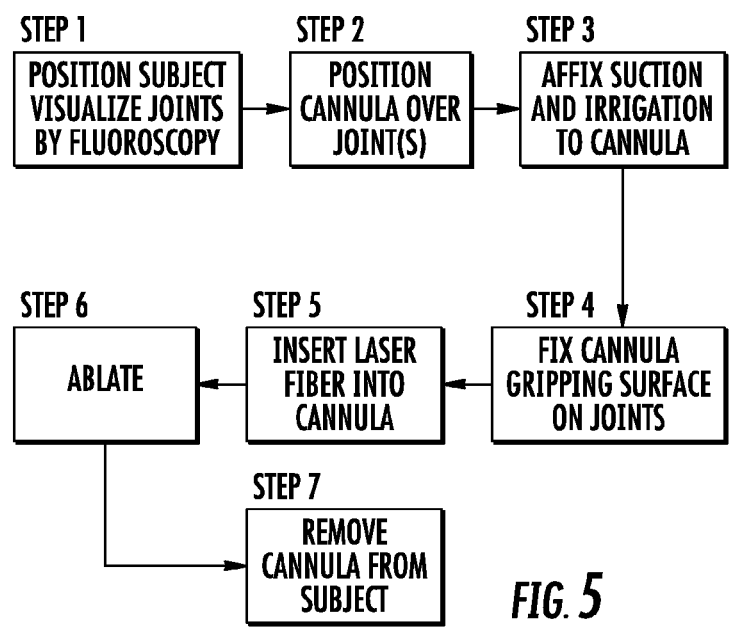

The invention also includes a method of using the visualizing ablation needle set in a surgical procedure for ablation of tissues in a subject's body. As an example of this procedure, a surgeon may achieve denervation of the pain-causing nerve fibers of the facet joints. The steps in a procedure for denervation of facet joints are shown diagrammatically in FIG. 5. Specifically, beginning in step 1, a subject in need of facet joint denervation can be brought to an operating room and placed in the prone position on a radiolucent table. A sterile preparation and drape is performed to the sites of the back to be treated.

A C-arm fluoroscope can be utilized to visualize the involved facet joints. Oblique projections can be used to visualize the ipsilateral side of the facet joints to be treated. Once a facet joint to be treated is identified in this manner, a local infiltrate of anesthetics (e.g. lidocaine with epinephrine) can be administered to the area. In step 2, a small scalpel can then be used to pierce the skin of the identified region. A cannula of a visualizing ablation needle set of the invention, with a trocar positioned within its lumen, can then be advanced through the skin and underlying muscle, and positioned on the facet joint. The position of the cannula can be photographed and viewed on the screen of the fluoroscope, and adjusted as necessary.

In step 3, suction and irrigation can be affixed to respectively different ports of the cannula and, once the position of the needle is satisfactory, in step 4 pressure can be placed on the cannula. A tissue-gripping surface on the cannula tip can ensure that the cannula, once contacting the facet joint, is stabilized in the appropriate position over the target joint. The trocar can then be disengaged and removed with the right hand while the cannula is held with the left hand. In step 4, a laser fiber connected to a laser energy source can then be passed into the cannula and fed through the cannula until substantial resistance is felt indicating placement of the laser fiber on the facet joint. Confirmation of proper placement of the needle set for facet denervation is now possible by fluoroscopy and, optionally, by direct visualization using the endoscopic camera.

With the cannula thus stabilized on the facet, in step 6, the ablation procedure can be carried out while the area of treatment is irrigated to cool from the action of the laser and outflow can be accomplished by way of the suction device. Duration and energy levels of the laser treatment can be varied according to the particular application. As the facet joint capsule with its associated nerve tissue is ablated, the capsule tissue can be clearly visualized and seen to shrink and disappear. The ability to visualize the extent of tissue ablation while applying the laser beam enables the surgeon to tailor the ablation procedure to the characteristics of individual subjects' facet tissues, thereby ensuring that ablation is both accurate and complete. Finally, in step 7, when the ablation procedure is seen to be satisfactory, the cannula can be removed from the subject.

Figure 7:
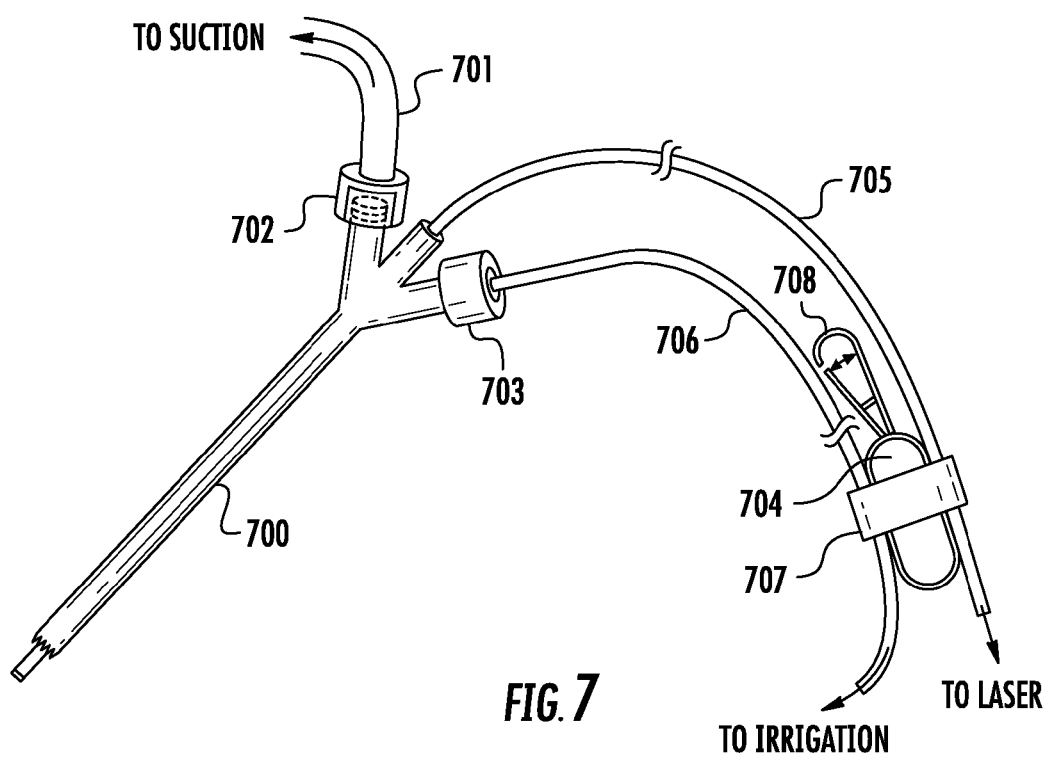

Turning now to FIG. 7, a perspective view of a dual port ablation needle kit with an irrigation and laser fiber aggregation point is shown. The kit can include a cannula shaft 700 with trocar (not shown) and dual ports extending from an exterior surface of the shaft 700 and providing a pathway into an interior portion of the shaft 700. A coupler 702 can be provided to couple to the shaft 700 a suction line 701 to a suction device, and a coupler 703 can be provided to couple to the shaft 700 an irrigation line 706 to an irrigation source. A laser fiber 705 additionally can be provided for placement through the shaft 700 and can be connected to a laser source. An aggregator 704 also can be provided as a plastic, fabric or nylon structure to which both the laser fiber 705 and the irrigation line 706 can be secured using a connector 707 such as a Velcro™ strap in order to coordinate the use of the laser fiber 705 and irrigation line 706 with the cannula. Optionally, a hanger 708 such as a hook, strap or carabiner can extend from the aggregator 704 to secure the aggregator 704 and thus the laser fiber 705 and irrigation line 706 to a gurney of the subject patient.

It should be noted that whereas certain exemplary embodiments of the visualizing ablation needle set and particular clinical applications have been discussed herein, the invention is not so limited, and its scope is to be determined according to the claims set forth below. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

We claim:
1. A dual port ablation cannula kit comprising:
a trocar;

a hollow shaft defining a longitudinal lumen, said shaft having a proximal segment and a distal segment, wherein said distal segment comprises a distal tip substantially aligned with the shaft to permit passage of the trocar within said hollow shaft, said distal tip being configured with a tissue-gripping surface wherein a plane of said tissue-gripping surface is substantially perpendicular to a longitudinal axis of said shaft;

dual ports extending from an exterior surface of the hollow shaft and each defining a hollow passageway into the hollow shaft;

dual couplers, one of the couplers coupling a suction line to one of the dual ports and another of the coupler coupling an irrigation line to another of the dual ports; and, a laser fiber comprising a diameter less than an interior diameter of the hollow shaft so as to permit passage of the laser fiber through the hollow shaft.

2. The kit of claim 1, wherein said proximal segment of said shaft is wider than said distal segment.

3. The kit of claim 1, wherein said proximal segment of said shaft is narrower than said distal segment.

4. The kit of claim 1, wherein said distal tip includes a plurality of triangularly shaped tissue-adhering irregular surfaces protruding from said tissue-gripping surface.

5. The kit of claim 4, wherein said tissue-adhering irregular surfaces are spaced apart on said tissue-gripping surface.

6. The kit of claim 4, wherein the triangularly shaped tissue-adhering irregular surfaces are angled inwardly towards a center point of the distal tip.

7. The kit of claim 4, further comprising an aggregator securing the laser fiber and suction line together.

8. The kit of claim 7, wherein the aggregator includes a hanger.

9. The kit of claim 7, wherein the aggregator includes a strap securing the laser fiber and suction line together.

* * * * *